United States Patent [19]
Takai et al.

[11] Patent Number: 6,013,348
[45] Date of Patent: Jan. 11, 2000

[54] LIQUID-PERMEABLE TOPSHEET IN DISPOSABLE BODY FLUIDS ABSORBENT GARMENT

[75] Inventors: Hisashi Takai; Junichi Noguchi, both of Ehime-ken; Tomoko Tsuji, Kagawa-ken, all of Japan

[73] Assignee: Uni-Charm Corporation, Ehime-ken, Japan

[21] Appl. No.: 09/013,920

[22] Filed: Jan. 27, 1998

[30] Foreign Application Priority Data

Jan. 31, 1997 [JP] Japan ................................. 9-053766

[51] Int. Cl.⁷ .............................. B32B 3/24; A61F 13/46
[52] U.S. Cl. ......................... 428/131; 428/132; 428/137; 428/163; 428/167; 604/378; 604/385.1
[58] Field of Search ..................... 428/167, 163, 428/131, 132, 137; 604/378, 385.1

[56] References Cited

U.S. PATENT DOCUMENTS

| | | | |
|---|---|---|---|
| 4,327,730 | 5/1982 | Sorensen | 128/287 |
| 5,268,213 | 12/1993 | Murakami et al. | 428/163 |
| 5,352,217 | 10/1994 | Curro | 604/378 |
| 5,368,910 | 11/1994 | Langdon | 428/137 |
| 5,387,209 | 2/1995 | Yamamoko et al. | 604/384 |
| 5,399,411 | 3/1995 | Suzuki et al. | 428/105 |
| 5,449,352 | 9/1995 | Nishino et al. | 604/383 |
| 5,514,105 | 5/1996 | Goodman, Jr. et al. | 604/370 |

FOREIGN PATENT DOCUMENTS

| | | |
|---|---|---|
| 0701805 | 3/1996 | European Pat. Off. . |
| 4-82977 | 3/1992 | Japan . |

*Primary Examiner*—William P. Watkins, III
*Attorney, Agent, or Firm*—Lowe Hauptman Gopstein Gilman & Berner

[57] ABSTRACT

A topsheet used in a disposable body fluids absorbent garment comprises a plurality of first ribs extending in parallel one to another in one direction and a plurality of second ribs extending in parallel one to another so as to intersect the first ribs. Each pair of adjacent first ribs intersect each pair of adjacent second ribs to define an air- and moisture-permeably opened region around which at least one of the respective pairs of adjacent first ribs and adjacent second ribs have their crests configured so that, between each pair of adjacent intersections of the first and second ribs each of the crests underlies an imaginary straight line connecting this pair of adjacent intersections.

3 Claims, 2 Drawing Sheets

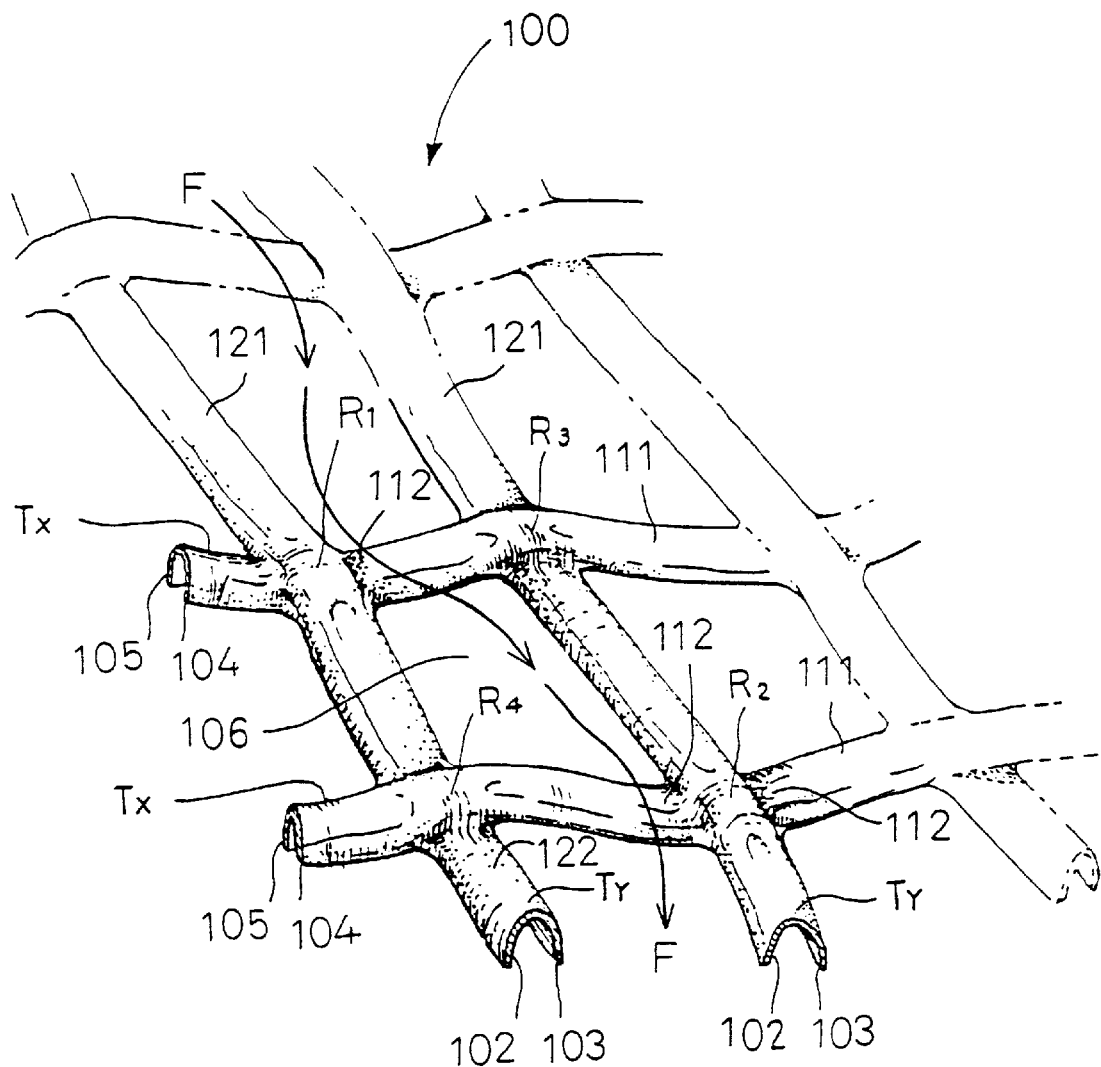

LIQUID-PERMEABLE TOPSHEET IN DISPOSABLE BODY FLUIDS ABSORBENT GARMENT

BACKGROUND OF THE INVENTION

This invention relates generally to a liquid-permeable topsheet used in a body fluids absorbent garment such as a disposable diaper, a sanitary napkin or the like.

FIG. 3 of the accompanying drawings is a perspective view exemplarily illustrating a topsheet 100 disclosed in Japanese Laid-Open Patent Application No. Hei4-82977. The topsheet 100 comprises a plurality of first ribs 111 extending in parallel one to another in one direction and a plurality of second ribs 121 extending in parallel one to another so as to intersect the first ribs 111. Each pair of adjacent the first ribs 111 intersect each pair of adjacent the second ribs 121 to define an air- and moisture-permeably opened region 106. The pair of first ribs 111 and the pair of second ribs 121 are in a relationship of warp and weft, i.e., the crests $T_x$ of the first ribs 111 protrude and the crests $T_y$ of the second ribs 121 descend at a pair of diagonally opposed intersections $R_3$, $R_4$. At another pair of diagonally opposed intersections $R_1$, $R_2$, the crests $T_y$ of the second ribs 121 protrude and the crests $T_x$ of the first ribs 111 descend so as to intersect the second ribs 121 at respective lower portions of their side surfaces. In this manner, the first and second ribs 111, 121 repeat their protruding and descending at a series of intersections arranged longitudinally in respective lines. With such topsheet 100, the ribs 111 protruding at the intersections $R_1$~$R_4$ are intended to be put in contact with the skin of a wearer, for example, at their crests $T_x$ and in the proximity thereof and the other ribs 121 having their crests descending at these intersections can be spaced apart from the skin of the wearer. Portions 112, 122 of the ribs spaced apart from the skin of the wearer define a serpentine or zigzag passage between the topsheet and the skin of the wearer as indicated by an arrow F and enable air and/or body fluids to move along the skin of the wearer.

Referring to FIG. 3, the portions 112 of the first ribs 111 intended to be spaced apart from the skin of the wearer, for example, between a pair of transversely adjacent second ribs 121, alternately appear with respect to the respective second ribs 121 so as to define the serpentine or zigzag passage for air and/or body fluids between these two ribs 121. Such serpentine or zigzag passage has a higher flow resistance than a non-serpentine passage and rather prevents air and/or body fluids from rapidly moving therethrough.

SUMMARY OF THE INVENTION

In view of the problem as has been described above, it is a principal object of the invention to provide a topsheet allowing air and/or body fluids to move rapidly between a wearer's skin and the topsheet.

The object set forth above is achieved, according to the invention, by a liquid-permeable topsheet used in a disposable body fluids absorbent garment adapted to be put in contact with the skin of a wearer and to absorb body fluids, said topsheet comprising:

a plurality of first ribs extending in parallel one to another in one direction and a plurality of second ribs extending in parallel one to another so as to intersect said first ribs, each of these ribs having an upper side intended to be put in contact with the skin of a wearer and a lower side opposed to said upper side, and each pair of adjacent said first ribs intersecting each pair of adjacent said second ribs to define an air- and moisture-permeably opened region around which at least one of said respective pairs of first and second ribs have respective crests configured in the same manner so that, between each pair of adjacent intersections of said first and second ribs, each of said crests underlies an imaginary straight line connecting said pair of adjacent intersections.

BRIEF DESCRIPTION OF THE DRAWINGS

FIG. 3 is a view similar to FIG. 2 showing a topsheet of prior art.

DESCRIPTION OF THE PREFERRED EMBODIMENT

Details of a topsheet used in a disposable body fluid absorbent garment according to the invention will be more fully understood from the description made with respect to sanitary napkin as a specific embodiment of the invention given hereunder in reference with the accompanying drawings.

Figure 1:
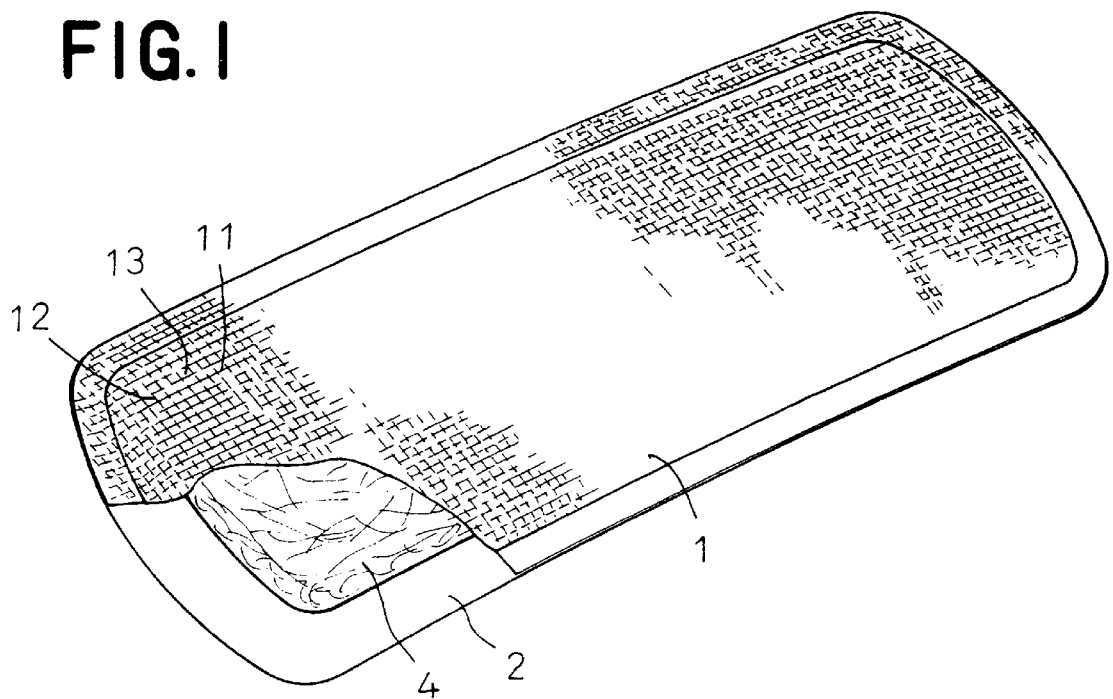
FIG. 1 is a perspective view showing a sanitary napkin or menstruation pad as partially broken away.

A sanitary napkin or menstruation pad shown by FIG. 1 in a fragmentary perspective view as partially broken away comprises a liquid-permeable topsheet 1, a liquid-impermeable backsheet 2, and a liquid-absorbent core 3 disposed between these two sheets 1, 2. The topsheet 1 and the backsheet 2 are identical to each other in shape as well as in size and placed one upon another. Over their portions extending outward beyond a peripheral edge of the absorbent core 3, these sheets 1, 2 are bonded together by means of heat-sealing or adhesive agent. The topsheet 1 is intended to be put in contact with the skin of a wearer in actual use of the sanitary napkin.

The topsheet 1 is formed from a thermoplastic synthetic resin film and has a plurality of first ribs 11 extending in parallel one to another longitudinally of the sanitary napkin as well as a plurality of second ribs 12 extending also in parallel one to another transversely of the sanitary napkin. Each pair of adjacent first ribs 11 intersects each pair of adjacent second ribs 12 to define a region 13 which is air-andmoisture-permeably opened.

The backsheet 2 is made of a thermoplastic synthetic resin film and the absorbent core 3 is formed from fluff pulp or a mixture of such fluff pulp and a hydrocolloid material.

Figure 2:
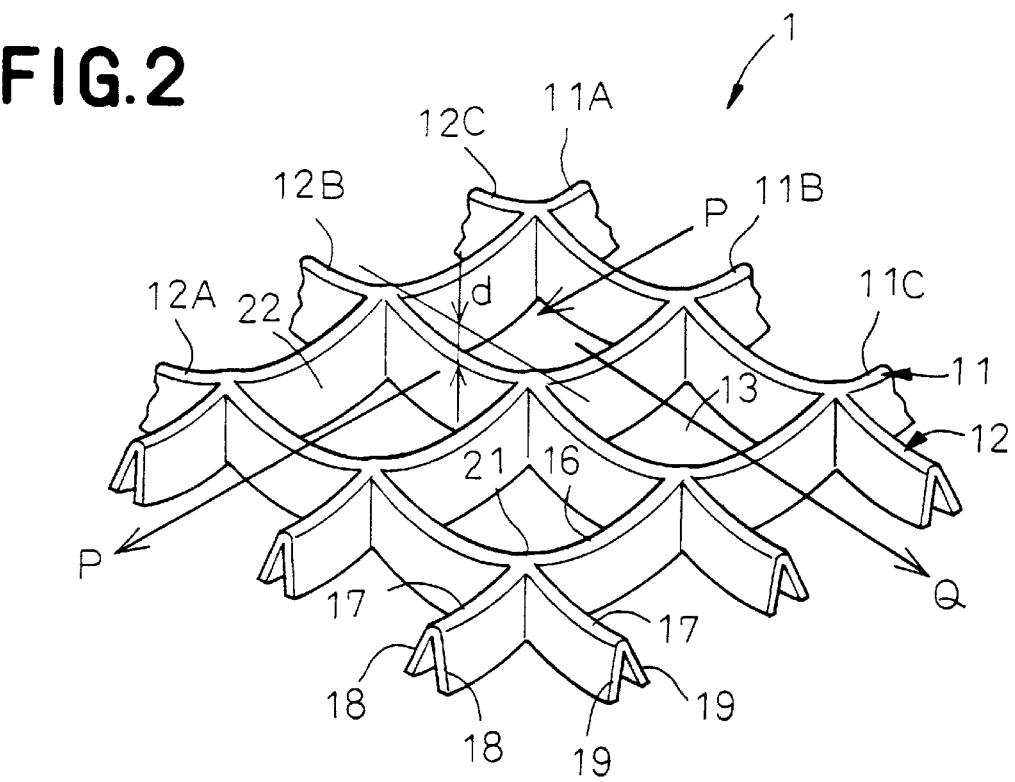
FIG. 2 is a fragmentary perspective view showing a topsheet in an enlarged scale.

FIG. 2 is a fragmentary perspective view showing the topsheet 1 in an enlarged scale. On the topsheet 1, the first and second ribs 11, 12 respectively have upper sides intended to be put in contact with the skin of a wearer and lower sides opposed to the upper sides, crests 16, 17 and side walls 18, 19 extending along the respective crests 16, 17 and diverging downward from the respective crests 16, 17. The crests 16, 17 of the first and second ribs 11, 12 intersect one another to form intersecting points 21 which define corners of the respective regions 13. The side walls 18, 19 are connected one to another along intersecting lines of the respective ribs 11, 12 so as to form tubular passages 22 extending toward the absorbent core 4. The pair of opposed side walls 18 and the pair of opposed side walls 19 present a U-shape cross-section, respectively, in other words, each of tubular passages 22 is tapered downward. The respective crests 16, 17 of the first and second ribs 11, 12 are curved or bent between each pair of adjacent intersections 21, 21 so as to be convex toward the absorbent core 4. The manner of such curves or bendings is substantially uniform between the respective pairs of adjacent first ribs as well as between the respective pairs of adjacent second ribs. However, the manner of such curves or bendings provided between the respective pairs of adjacent first ribs 11 may be the same as or different from the manner of such curves or bendings provided between the respective pairs of adjacent second ribs 12.

When the sanitary napkin is horizontally placed with the topsheet 1 upside, the intersections 21 of the first and second ribs 11, 12 lie at the uppermost level. With the sanitary napkin put on a wearer, the crests 16, 17 of the first and second ribs 11, 12 come in contact with the skin of a wearer in the proximity of these intersections 21, leaving the remaining curves (or bendings) spaced apart from the skin of the wearer. As illustrated, the first ribs 11 extending in parallel one to another transversely of the sanitary napkin and the second ribs 12 extending in parallel one to another longitudinally of the sanitary napkin are curved or bent in the same manner. So far as these curved or bent portions of the ribs 11, 12 are spaced apart from the skin of the wearer, therefore, passages for linear movement of air and/or body fluids are formed as indicated by arrows P, Q. Such linear passages advantageously allow air and/or body fluids to move more rapidly than serpentine or zigzag passages. Rapid movement of air contributes to improvement of air-permeability desired between the skin of the wearer and the sanitary napkin. Rapid movement of body fluids facilitates spread thereof over the topsheet and thereby allows the absorbent core 4 to be effectively used over its area as large as possible. It should be remembered that the sanitary napkin is required to have a high spot-absorptivity. Such requirement is well satisfied by the open regions 13 defining respective tubular passages 22. The tubular passages 22 are effective to transfer body fluids to the absorbent core 4 under their capillary effect and, if desired, lower ends of the respective tubular passages 22 may be applied with suitable hydrophilicity imparting agent to improve an efficiency of these tubular passages 22. However, after the spot absorption has locally saturated the absorbent core 4 with body fluids, it is required to make the remaining quantity of body fluids spread over the topsheet 1 so that a surplus ability of the absorbent core 4 may be used. This requirement can be satisfied by an adaptability of the topsheet 1 for spreading of body fluids.

The topsheet 1 can be formed by pressing a heated polyethylene film against a mold of the corresponding configuration under vacuum and/or pressurized air. If it is desired to use the topsheet 1 for sanitary napkin or disposable diaper, the first and second ribs 11, 12 may be preferably dimensioned as follows: each crest 16, 17 is 0.2 ~5 mm wide, each pair of adjacent ribs 16, 17 are spaced apart from each other by a distance of 0.3~7 mm, each side wall 18, 19 is 0.3~3 mm high in the proximity of the intersection 21, and the first and second ribs 11, 12 are curved or bent so as to be spaced apart from a straight line connecting each pair of adjacent intersections 21 by a distance d (See FIG. 2) of 0.1~1 mm, more preferably 0.2~1 mm.

While the first and second ribs 11, 12 are shown as intersecting each other at a right angle, they may also obliquely intersect each other. An alternative arrangement is also possible in which one of the first and second ribs 11, 12 are curved or bent and the other extend horizontally. According to the specific embodiment shown by FIG. 2, the second ribs 12 are curved or bent in the same shape so far as the second ribs 12A, 12B, 12C extending between the first ribs 11A and 11B are concerned. Similarly, the second ribs 12A, 12B, 13C extending between the first ribs 11B and 11C are curved or bent in the same shape. It should be understood that the respective second ribs extending between the first ribs 11A and 11B may have the same shape as the shape of the respective second ribs extending between the first ribs 11B and 11C. This is true a also for the shape in which the first ribs 11 are curved or bent.

The liquid-permeable topsheet according to the invention comprises a plurality of ribs extending in parallel one to another and allows air and/or body fluids to linearly move in parallel to the ribs. The body fluids absorbent garment using such topsheet is excellent in air-permeability between the topsheet and the skin of the wearer, on one hand, and in spreadability of body fluids on the topsheet, on the other hand.

What is claimed is:

1. A liquid-permeable topsheet used in a disposable body fluids absorbent garment adapted to be put in contact with the skin of a wearer and to absorb body fluids, the topsheet comprising:

a plurality of first ribs extending in parallel one to another in one direction and a plurality of second ribs extending in parallel one to another so as to intersect said first ribs, each of these ribs having an upper side intended to be put in contact with the skin of a wearer and a lower side opposed to said upper side, and each pair of adjacent said first ribs intersecting each pair of adjacent said second ribs to define an air- and moisture-permeably opened region around which at least one of said respective pairs of first and second ribs have respective crests configured in the same manner so that, between each pair of adjacent intersections of said first and second ribs, each of said crests underlies an imaginary straight line connecting said pair of adjacent intersections.

2. A liquid-permeable topsheet according to claim 1, wherein said first and second ribs have side walls extending downward from said upper sides to said lower sides to form liquid-passages serving to guide said body fluids into said garment in said opened regions.

3. A liquid-permeable topsheet according to claim 1, wherein each of said crests is 0.2~5 mm wide, each pair of adjacent said first ribs and each pair of adjacent said second ribs are spaced apart from each other by a distance of 0.3~7 mm, each of said side walls is 0.3~3 mm high in the proximity of said intersection, and each of said crests underlies said imaginary straight line by a distance of 0.1 ~1 mm.

* * * * *